US010927668B2

(12) United States Patent
Iyer et al.

(10) Patent No.: US 10,927,668 B2
(45) Date of Patent: Feb. 23, 2021

(54) METHODS AND APPARATUS FOR THE DOWNHOLE ANALYSIS OF THE COMPOSITION OF FORMATION GASES

(71) Applicant: SCHLUMBERGER TECHNOLOGY CORPORATION, Sugar Land, TX (US)

(72) Inventors: Jaisree Iyer, Cambridge, MA (US); Terizhandur S. Ramakrishnan, Boxborough, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 215 days.

(21) Appl. No.: 16/215,341

(22) Filed: Dec. 10, 2018

(65) Prior Publication Data
US 2019/0107523 A1 Apr. 11, 2019

Related U.S. Application Data

(62) Division of application No. 14/560,389, filed on Dec. 4, 2014, now Pat. No. 10,151,738.

(51) Int. Cl.
*E21B 47/135* (2012.01)
*E21B 47/07* (2012.01)
(Continued)

(52) U.S. Cl.
CPC ............ *E21B 47/135* (2020.05); *E21B 47/06* (2013.01); *E21B 47/07* (2020.05); *E21B 47/10* (2013.01);
(Continued)

(58) Field of Classification Search
CPC ........ G01N 21/01; G01N 21/31; G01N 21/35; G01N 21/3504; G01N 21/359; G01N 33/00; G01N 33/0004; G01N 33/0011; G01N 33/0036; G01N 33/007; G01N 33/0073; G01N 33/24; G01N 33/241; G01N 2033/243; G01N 2033/245; E21B 47/00; E21B 47/01; E21B 47/04; E21B 47/06; E21B 47/07; E21B 47/10; E21B 47/107;
(Continued)

(56) References Cited
U.S. PATENT DOCUMENTS 4,994,671 A 2/1991 Safinya et al.
5,167,149 A 12/1992 Mullins et al.
(Continued)

OTHER PUBLICATIONS

Alkasab, et al., "An apparatus for measuring adiabatic and isothermal Joule-Thomson coefficients at low temperatures", Review of Scientific Instruments, vol. 44, No. 11, 1973, pp. 1561-1566.
(Continued)

*Primary Examiner* — Cheung Lee
(74) *Attorney, Agent, or Firm* — Trevor G. Grove

(57) ABSTRACT

Methods and apparatus are provided for determining downhole the composition of natural gas from a formation. Some methods include downhole measurements of the near-infrared spectra and the Joule-Thomson coefficient of the gas, and processing the results of the downhole measurements in order to obtain a determination of the amounts of a plurality of natural gas components such as $CH_4$, $C_2H_6$, $CO_2$, $N_2$, and $H_2S$.

13 Claims, 5 Drawing Sheets

(51) Int. Cl.
*E21B 47/06* (2012.01)
*E21B 47/10* (2012.01)
*G01N 33/00* (2006.01)
*E21B 49/08* (2006.01)

(52) U.S. Cl.
CPC ...... *G01N 33/0036* (2013.01); *E21B 49/0875* (2020.05)

(58) Field of Classification Search
CPC ...... E21B 47/11; E21B 47/113; E21B 47/117; E21B 47/12; E21B 47/13; E21B 47/135; E21B 47/26; E21B 49/0875
See application file for complete search history.

(56) References Cited

U.S. PATENT DOCUMENTS

| | | | |
|---|---|---|---|
| 5,201,220 A | 4/1993 | Mullins et al. | |
| 5,266,800 A | 11/1993 | Mullins | |
| 5,331,156 A | 7/1994 | Hines et al. | |
| 5,859,430 A * | 1/1999 | Mullins | E21B 49/10 250/255 |
| 7,126,332 B2 | 10/2006 | Blanz et al. | |
| 7,520,158 B2 | 4/2009 | DiFoggio | |
| 8,519,713 B2 | 8/2013 | Lawrence et al. | |
| 2007/0119244 A1 | 5/2007 | Goodwin et al. | |
| 2010/0148780 A1 | 6/2010 | Lawrence et al. | |
| 2011/0029273 A1 | 2/2011 | Lovell | |
| 2011/0042070 A1 | 2/2011 | Hsu et al. | |
| 2012/0053838 A1 | 3/2012 | Andrews et al. | |
| 2012/0055242 A1 | 3/2012 | Tustin et al. | |
| 2014/0326063 A1 | 11/2014 | Lovell et al. | |

OTHER PUBLICATIONS

Bullin, et al., "Composition Variety Complicates Processing Plans for US Shale Gas", Oil and Gas Journal, vol. 107, 2009, pp. 50-55.
Dong, et al., "New Downhole Fluid Analysis Tool for Improved Reservoir Characterization", SSPE 108566—Offshore Europe, Aberdeen, Scotland, UK, Dec. 2008, pp. 1107-1116.
Fujisawa, et al., "Near-Infrared Compositional Analysis of Gas and Condensate Reservoir Fluids at Elevated Pressures and Temperatures", Applied Spectroscopy, vol. 56, No. 12, 2002, pp. 1615-1620.
Hea, "Hydrocarbon wetness, NGL, and sulphur byproducts of natural gases in western Canada", Technical Report 2352, Geological Survey of Canada, Apr. 1991.
Hecht, "Measurement of the joule-thomson coefficient", Journal of Chemical Education, Oct. 1954, pp. 530-533.
Lemmon, et al., "NIST Reference Fluid Thermodynamic and Transport Properties Database", (REFPROP): Version 8.0, 2007, 57 pages.
Moulijn, et al., "Chemical Process Technology", 2nd Edition, ISBN: 978-1-4443-2025-1, May 2013, 2012, 566 pages.
Randelman, et al., "Joule-Thomson coefficients of hydrogen and methane mixtures", Journal of Chemical & Engineering Data, vol. 33, No. 3, 1988, pp. 293-299.
Van Agthoven, et al., "Near-Infrared Spectral Analysis of Gas Mixtures", Applied Spectroscopy, vol. 56, No. 5, 2002, pp. 593-598.
Rojey, et al., "Natural Gas Production Processing Transport", ISBN-13: 978-2710806936, Institut Franpcais Du Pbetrole Publications, Jan. 1997, 429 pages.
International Search Report for corresponding PCT Application Serial No. PCT/201506367 dated Feb. 16, 2016, 3 pages.

* cited by examiner

METHODS AND APPARATUS FOR THE DOWNHOLE ANALYSIS OF THE COMPOSITION OF FORMATION GASES

The present application is a divisional of U.S. application Ser. No. 14/560,389, filed Dec. 4, 2014, which is hereby incorporated herein by reference in its entirety.

TECHNICAL FIELD

The subject disclosure relates to the hydrocarbon industry. More particularly, the subject disclosure relates to apparatus and methods for evaluating down-hole the composition of formation gases.

BACKGROUND

Natural gas reserves include hydrocarbon components such as methane ($CH_4$), ethane ($C_2H_6$), propane ($C_3H_8$), and butane ($C_4H_{10}$), and inorganics such as carbon dioxide ($CO_2$), hydrogen sulfide ($H_2S$), nitrogen ($N_2$), oxygen ($O_2$), and helium (He). The composition of the gas reserves varies with the source type. Associated gas reserves have lower concentrations of inorganic components, such as $CO_2$, $H_2S$, and $N_2$, than non-associated or shale gas reserves.

Table 1 (taken from multiple sources such as Bullin, K. A. and Krouskop, P. E., "Compositional variety complicates processing plans for US shale gas", Oil and Gas Journal, Vol. 107, pp. 50-55 (2009), Moulijn, J. A., et al., Chemical Process Technology, John Wiley and Sons Ltd., Somerset, N.J., USA (2013), Rojey, A., et al., Natural gas production processing transport, Editions Technip, Paris, France (1997), and Hea, J. P., "Hydrocarbon wetness, NGL, and sulphur byproducts of natural gases in western Canada", Technical Report 2352, Geological Suvery of Canada (April 1991)) shows the range of concentrations for the five major components in natural gas reservoirs. For pricing purposes, it is useful to determine the composition-dependent heat of combustion of the varied gases.

TABLE 1

All values are in volume %, except for $C_2H_6$ concentration in non-associated gas, which is given in mole %

| Constituents | Associated gas | Non-associated gas | Shale gas |
|---|---|---|---|
| $CH_4$ | 44-83 | 27-97 | 27-97 |
| $C_2H_6$ | 8-21 | 0-15 | 0-16 |
| $CO_2$ | 0-9 | 0-54 | 0-10 |
| $N_2$ | 0-3 | 0-26 | 0-65 |
| $H_2S$ | 0-3 | 0-36 | — |

Downhole gas composition determines the calorific value of the gas reserves; but data on the spatial variability of gas composition is also important for developing zonal production strategies. Additionally, information on the presence of corrosive gases such as $H_2S$ and $CO_2$ are desirable for the design and specification of completion and production hardware. Traditionally, the gas composition is determined by sampling down-hole followed by surface laboratory analysis such as gas chromatography. Surface analysis is relatively expensive and slow, and sample integrity has to be ensured in storage. The number of samples that can be transported to the surface is also limited.

Several technologies have been proposed to carry out the downhole compositional analysis of gases. These include technologies based on (near) infrared spectroscopy (see, U.S. Pat. No. 4,994,671 to Safinya et al., U.S. Pat. No. 5,167,149 to Mullins et al., U.S. Pat. No. 5,201,220 to Mullins et al., U.S. Pat. No. 5,266,800 to Mullins et al., U.S. Pat. No. 5,331,156 to Hines et al., U.S. Pat. No. 5,859,430 to Mullins et al., all of which are hereby incorporated by reference herein in their entireties), photoacoustic spectroscopy (see, U.S. Pat. No. 7,520,158 to DiFoggio which is hereby incorporated by reference herein in its entirety), mass spectroscopy, gas chromatography (see U.S. Patent Application Publication No. 2012/0053838 to Andrews et al., which is hereby incorporated by reference herein in its entirety), nuclear magnetic resonance (see U.S. Pat. No. 7,126,332 to Blanz et al., which is hereby incorporated by reference herein in its entirety), and electrochemistry (see, U.S. Pat. No. 8,519,713 to Lawrence et al., which is hereby incorporated by reference herein in its entirety). The most successful of these technologies has been infrared absorption spectroscopy as deployed in the downhole fluid analyzer (DFA) tool of Schlumberger.

The DFA uses two spectrometers with twenty and sixteen channels spanning wavelengths of 400-2100 nm and 1600-1800 nm respectively. Using absorption spectra, the DFA tool can determine the approximate relative fractions of methane, ethane, carbon dioxide, and the collective composition of all other hydrocarbons in the gas stream. See, Dong, C., et al., "New downhole-fluid-analysis tool for improved reservoir characterization", SPE Reservoir Evaluation and Engineering 11(6), pp. 1107-1116 (2008). The limitation of infrared spectroscopy is that the composition of homonuclear diatomic molecules, e.g., nitrogen, oxygen, hydrogen, and inert gases such as helium cannot be determined. These gases are substantially infrared inactive.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In accordance with some example embodiments, a method of analyzing down-hole in a formation a formation gas sample includes: storing portions of the formation gas sample in first and second downhole chambers of a downhole tool at respective first and second initial pressures; flowing at least a portion of the formation gas sample through at least one of (a) porous element in the downhole tool and (b) a throttling valve in the downhole tool, while permitting the first and second initial pressures to vary, where the first chamber is upstream the porous element and the second chamber is downstream the porous element; measuring respective upstream and downstream temperatures and respective upstream and downstream pressures; and using the respective upstream and downstream temperatures and respective upstream and downstream pressures to determine a Joule-Thomson coefficient ($\eta$) for the gas sample.

In accordance with some example embodiments, a system for investigating gas from a formation traversing a borehole includes: a selectively extendible fluid admitting assembly configured to selectively isolate a portion of a wall of the borehole and establish fluid communication with the formation; first and second chambers in fluid communication with the fluid admitting assembly, the first and second chambers configured to receive a gas sample from the fluid admitting assembly; at least one of (a) a porous element and (b) a throttling valve, in fluid communication with the first and second chambers, wherein the first chamber is upstream of the at least one of (a) a porous element and (b) a throttling valve and the second chamber is downstream of the at least one of (a) a porous element and (b) a throttling valve; an upstream pressure sensor fluidly coupled to the first chamber and configured to provide upstream pressure readings; a downstream pressure sensor fluidly coupled to the second chamber and configured to provide downstream pressure readings; an upstream temperature sensor coupled to the upstream chamber and configured to provide upstream temperature readings; a downstream temperature sensor coupled to the second chamber and configured to provide downstream temperature readings; control valves disposed between the at least one of (a) a porous element and (b) a throttling valve and the first and second chambers and between the first and second chambers and the fluid admitting assembly; and a processor configured to generate a determination of a Joule-Thomson coefficient ($\eta$) for the gas sample utilizing the readings from the upstream pressure sensor, the downstream pressure sensor, the upstream temperature sensor and the downstream temperature sensor.

In accordance with some examples, a system for investigating gas from a formation traversing a borehole includes: a borehole tool including a fluid admitting assembly configured to selectively isolate a portion of a wall of the borehole and establish fluid communication with the formation, an optical fluid analyzer in fluid communication with the fluid admitting assembly, the optical fluid analyzer configured to utilize a near infrared spectrum to analyze a gas sample obtained from the fluid admitting assembly, and a Joule-Thomson coefficient analyzer including first and second chambers in fluid communication with the fluid admitting assembly, at least one of (a) a porous element and (b) a throttling valve, in fluid communication with the first and second chambers, pressure sensors coupled to the first and second chambers, temperature sensors coupled to the first and second chambers, and control valves coupled between the porous element and the first and second chambers and between the first and second chambers and the fluid admitting assembly; and at least one processor coupled to the Joule-Thomson coefficient analyzer and to the optical fluid analyzer and configured to (i) utilize readings from the pressure sensors and the temperature sensors to generate a determination of a Joule-Thomson coefficient (for the gas sample, (ii) find concentrations of methane ($CH_4$), ethane ($C_2H_6$) and carbon dioxide ($CO_2$) in the gas sample, and (iii) generate an indication of the concentration or mole fraction of at least one of hydrogen sulfide ($H_2S$) and nitrogen ($N_2$).

In accordance with some examples, a system for investigating gas from a formation traversing a borehole includes: a borehole tool including (i) a fluid admitting assembly adapted to selectively isolate a portion of a wall of the borehole and establish fluid communication with the formation, (ii) an optical fluid analyzer in fluid communication with the fluid admitting assembly, the optical fluid analyzer configured to utilize a near infrared spectrum to analyze a gas sample obtained from the fluid admitting assembly, (iii) a Joule-Thomson coefficient analyzer including first and second chambers in fluid communication with the fluid admitting assembly, (iv) at least one of (a) a porous element and (b) a throttling valve, in fluid communication with the first and second chambers, (v) pressure sensors coupled to the first and second chambers, (vi) temperature sensors coupled to the first and second chambers, and (vii) control valves coupled between the porous element and the first and second chambers and between the first and second chambers and the fluid admitting assembly; and at least one processor coupled to the Joule-Thomson coefficient analyzer and to the optical fluid analyzer, the at least one processor being configured to (i) utilize readings from the pressure sensors and the temperature sensors and generate a determination of a Joule-Thomson coefficient ($\eta$) for the gas sample, and (ii) find a concentration and a mole fraction of at least one of methane ($CH_4$), ethane ($C_2H_6$), carbon dioxide ($CO_2$), hydrogen sulfide ($H_2S$) and nitrogen ($N_2$).

In accordance with some examples, a method for determining down-hole the composition of natural gas from a formation includes a downhole measurement of the near-infrared spectrum and the Joule-Thomson coefficient of the gas, and processing the results of the downhole measurements in order to obtain a determination of the amounts of $CH_4$, $C_2H_6$, $CO_2$, $N_2$, and $H_2S$ in the gas.

In accordance with some examples, an apparatus for determining down-hole the composition of natural gas from a formation includes a formation testing tool including a fluid admitting assembly, a near-infrared optical fluid analyzer, a device for measuring Joule-Thomson coefficient, and one or more processors. The optical fluid analyzer is utilized to obtain indications of the amount of $CH_4$, $C_2H_6$, $CO_2$ in a gas sample obtained by the fluid admitting assembly. The Joule-Thomson coefficient analyzer includes two chambers that store formation gases obtained by the fluid admitting assembly, a porous element, upstream and downstream temperature sensors, upstream and downstream pressure sensors, and flow control elements such as valves. The flow control elements and the chambers are adapted to cause gas stored in one chamber at a first pressure to flow through the porous element to the other chamber, and the differences in measured pressures and temperatures are utilized to obtain a Joule-Thomson coefficient determination for the gas. With the information from the optical fluid analyzer and the Joule-Thomson coefficient analyzer, the processor(s) generates a determination of the amounts of $N_2$ and $H_2S$ in the gas.

Additional aspects, embodiments, objects and advantages of the disclosed methods may be understood with reference to the following detailed description taken in conjunction with the provided drawings.

DETAILED DESCRIPTION

In one aspect, many natural gases from geological formations comprise one or more of $CH_4$, $C_2H_6$, $CO_2$, $N_2$, and $H_2S$. While apparatus and methods are known for downhole determination of the presence and concentrations of $CH_4$, $C_2H_6$, and $CO_2$ using the near-infrared spectra, these apparatus and methods are ineffective in measuring and determining the amounts of $N_2$ and $H_2S$ in the gas.

Before turning to specific embodiments, a description of the underyling physics utilized by the embodiments may be helpful. In particular, the Joule-Thomson coefficient η of a gas is defined as the isenthalpic change (constant enthalpy H) of temperature T, with respect to pressure P. The fundamental equation for a multicomponent gas system is of the form $U=U(S, V, N_i)$, where U is the internal energy, S is the entropy, V is the volume, and $N_i$ is the number of moles of component i of the gas. By definition, $T=\partial U/\partial S$, $P=-\partial U/\partial V$, and $H=U+PV$. Given that U, V, and S are first order homogeneous extensive quantities with respect to $N=\Sigma_i N_i$, and that $C_p$, the specific heat at constant pressure, and $x_i$ (mole fraction) are positive, it can be shown that $$T = \tilde{T}\left(P, \frac{H}{N}, x_i\right) = \tilde{T}(P, h, x_i),$$

i.e., T may be expressed as a function of pressure, molar enthalpy $h=H/N$, and the mole fraction of the gas components. By definition, the Joule-Thomson coefficient η is $$\eta = \partial \tilde{T}/\partial P \quad (1)$$

Figure 1A:
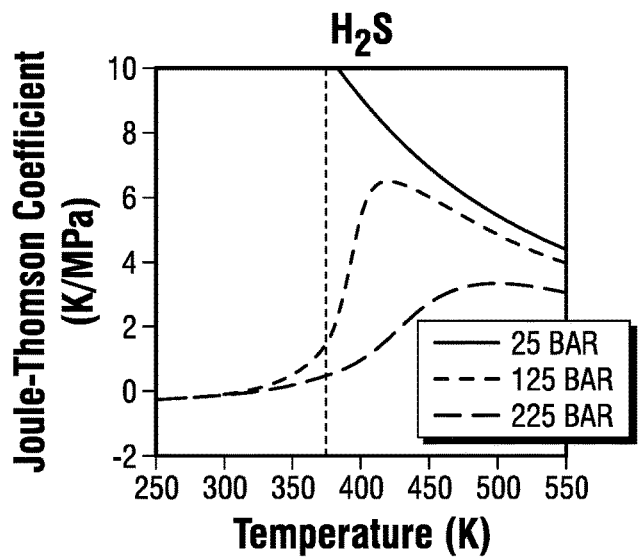
FIGS. 1a and 1b are plots of the Joule-Thomson coefficient as a function of temperature for hydrogen sulfide and nitrogen respectively.
Figure 1B:
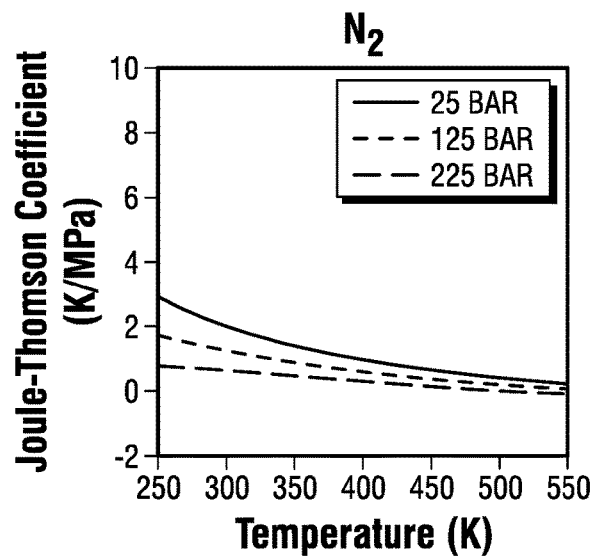

The Joule-Thomson coefficient n delineates some components in a gas stream more effectively than measurements of gas density (ρ), viscosity (μ), and specific heat ($C_p$). For example, for a given T and P, sufficiently away from the critical point, gases with similar molecular weight have nearly the same ρ, but may differ in η. Furthermore, η takes on both positive and negative values, with a strong pressure dependence, as illustrated parametrically in FIGS. 1a and 1b. In particular, for three different pressures, FIG. 1a shows the variation of η for $H_2S$, while FIG. 1b shows the variation of η for $N_2$, borh with resepect to temperature. A comparison of FIGS. 1a and 1b reveals entirely different pressure dependencies of η for the two gases. In addition, at the temperatures of relevance, the numerical value of η is enough to distinguish between the two gases.

For a gas-stream, η is measured by flowing gas through an insulated porous plug or a throttling valve and measuring upstream and downstream pressures and temperatures. The ratio of the temperature difference to the pressure difference is equal to the Joule-Thomson coefficient, because the flow is nearly isenthalpic. Since η varies with pressure and temperature, effort is taken to keep the flow rate small enough for the ratio to be unaffected by the magnitude of the pressure difference. At the same time, the flow rate should have a large enough magnitude for the temperature changes to be resolved. Since η has a magnitude of 1 K $MPa^{-1}$, for reasonable accuracy, about a one to two MPa pressure drop may be used in the flowing gas stream on an inlet gas stream at a few tens of MPa in pressure.

Figure 2:
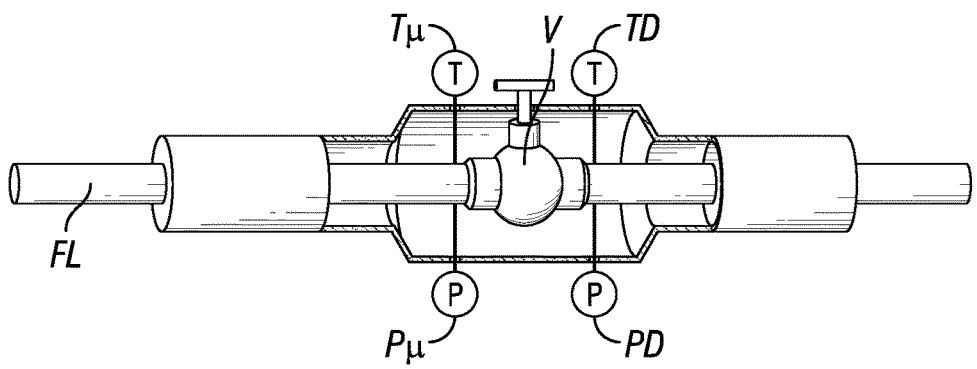
FIG. 2 is a schematic of an experimental arrangement for the measurement of the Joule-Thomson coefficient.

A schematic of an experimental setup that could be used to measure the Joule-Thomson coefficient of a gas stream is shown in FIG. 2 and includes a flow line FL, insulation I around a portion of the flow line, a throttling valve V located in the insulated portion of the flow line FL, upstream temperature and pressure sensors, TU and PU respectively, located in the insulated portion of the flow line, and downstream temperature and pressure sensors TD and PD respectively, located in the insulated portion of the flow line. As discussed hereinafter with reference to FIG. 6, in a downhole tool a similar arrangement can be provided by attaching an adiabatic throttling valve or a porous plug within the insulated flowline such that steady state temperature and pressure differences may be measured across the valve or the plug.

To determine whether the Joule-Thomson coefficient could be used to find the presence and concentrations of $N_2$ and $H_2S$ in a gas stream using an apparatus such as shown in FIG. 2, a calculation of η was first made for several natural gas mixtures having temperatures, pressures, and compositions similar to those found in gas reservoirs. Accurate η measurement is difficult because of the small temperature differences compared to the accuracy of temperature sensors. Therefore, conservatively, a normally distributed error of 10% to the reported values of η was added i.e., the value of η used in the calculations was obtained from a Gaussian distribution centered at the η obtained from REFPROP (the National Institute of Standards and Technology (NIST) Reference Fluid Thermodynamic and Transport Properties Database Version 8.0), with a standard deviation of 10%. Then, an assumption was made that near-infrared absorption measurements can be used to determine the molar concentrations of $CH_4$, $C_2H_6$, and $CO_2$. Because these measurements do not provide exact results, a probability density function (PDF) of the errors in the concentration measurements of $CH_4$, $C_2H_6$, and $CO_2$ from near-infrared absorption would be added. In the illustrative example, as an approximation, distributed error was added to the mole fraction because that error was specified in the data. For each of the three gases, the mole fraction errors allow the calculation of the synthetic concentration measurements, provided the total concentration had no errors. The synthetic concentrations are the product of the total concentration and the mole fractions. The PDFs were generated from the data reported by Fujisawa et al. (see, Fujisawa, G., et al., "Near-infrared compositional analysis of gas and condensate reservoirs fluids at elevated pressures and temperatures", Applied Spectroscopy 56(12) pp. 1615-1620 (2002)) and van Agthoven et al. (see, van Agthoven, M. A., et al., "Near-infrared spectral analysis of gas mixtures", Applied Spectroscopy 56(5) pp. 593-598 (2002)) and are tabulated in Table 2. Note that the concentration of "higher" hydrocarbons (i.e., propane, butane, etc.) are not included in Table 2 because these are often not relevant for the mixtures considered here. To use the information in Table 2, three separate Gaussian distribution functions were fitted to the errors associated with the $CH_4$, $C_2H_6$, and $CO_2$ mole fractions, although calculations could have been carried out with concentrations if error specification had been available. The mean and standard deviation of the Gaussian distribution for the errors in $CH_4$, $C_2H_6$, and $CO_2$ mole fractions were −1.25% and 4.32%, −2.43% and 21.17% and 11.54% and 12.32%, respectively; however, if the computed mole fractions as measurement substitutes became negative, they were set to zero. From Table 2, it is evident that the error in the concentration measurement depends on the mole fraction value, with higher errors typically associated with lower mole fractions. In the absence of sufficient information, this mole fraction dependency of the error was not incorporated in the calculations.

TABLE 2

All numbers stated in percentages including errors.

| $x_{CH_4}$ | $x_{C_2H_6}$ | $x_{CO_2}$ | $\varepsilon_{CH_4}$ | $\varepsilon_{C_2H_6}$ | $\varepsilon_{CO_2}$ |
|---|---|---|---|---|---|
| 10 | 10 | 20 | 0.00 | 0.00 | 20.00 |
| 25 | 0 | 75 | −9.60 | — | 3.87 |
| 25 | 0 | 75 | 8.00 | — | −2.67 |
| 41 | 0 | 0 | 0.00 | — | — |
| 45 | 12 | 20 | −4.44 | −8.33 | 20.00 |
| 50 | 0 | 50 | −8.60 | — | 9.60 |

TABLE 2-continued

All numbers stated in percentages including errors.

| $x_{CH_4}$ | $x_{C_2H_6}$ | $x_{CO_2}$ | $\varepsilon_{CH_4}$ | $\varepsilon_{C_2H_6}$ | $\varepsilon_{CO_2}$ |
|---|---|---|---|---|---|
| 50 | 0 | 50 | 2.00 | — | −4.00 |
| 64 | 12 | 20 | −4.38 | −6.67 | 21.5 |
| 64 | 12 | 20 | −3.13 | −16.67 | 10.00 |
| 70 | 0 | 0 | −1.43 | — | — |
| 75 | 0 | 25 | −5.33 | — | 17.60 |
| 75 | 0 | 0 | −6.67 | — | — |
| 75 | 10 | 0 | 1.33 | 20.00 | — |
| 75 | 10 | 0 | 0.00 | 0.00 | — |
| 78 | 6 | 0 | 6.41 | 33.33 | — |
| 80 | 15 | 0 | 1.63 | −1.33 | — |
| 80 | 15 | 0 | 0.00 | −13.33 | — |
| 82 | 0 | 0 | 0.00 | — | — |
| 88 | 10 | 0 | 0.00 | −18.00 | — |
| 88 | 10 | 0 | −1.14 | −10.00 | — |
| 90 | 0 | 0 | 0.00 | — | — |
| 95 | 5 | 0 | −0.21 | −44.00 | — |
| 95 | 5 | 0 | −1.05 | 0.00 | — |

Using the mixture Joule-Thomson coefficient as computed from REFPROP at the T and P of interest, a noise value is added to η as a measurement substitute. The $CH_4$, $C_2H_6$, and $CO_2$ concentrations as measurement substitutes are also known. The $H_2S$ and $N_2$ concentrations were then determined using REFPROP's model for Joule-Thomson coefficient of gaseous mixtures. More particularly, the concentrations of the constituents of the gas stream may be expressed according to $C_i = Cx_i$, where $x_i$ is the mole fraction of the species i, and C is the total number of moles per unit volume, also called (total) concentration. These x, are unknowns for the species $CH_4$, $C_2H_6$, $CO_2$, $H_2S$, and $N_2$. For assumed values of these such that $\Sigma_i x_i = 1$, reference software such as REFPROP may be used to predict the Joule-Thomson coefficient as a function of T, P, and $x_i$. The final consideration is the total number of molecules per unit volume, i.e., the concentration. A compressibility factor Z for a given set of T, P, and x may be calculated using a package such as REFPROP. Knowing the compressibility factor from PV=nZRT, the total concentration $$C = n/V = P/ZRT \quad (2)$$

is obtained, where R is the gas constant.

Given the measurements η, T, P and the spectroscopic determination of the concentrations of methane, ethane, and carbon dioxide, the concentrations of $H_2S$ and $N_2$ are obtained as follows. First, using REFPROP, an estimated Joule-Thomson value $\tilde{\eta}$ (a function) may be constructed as $$\tilde{\eta}(T, P, x_{CH_4}, x_{C_2H_6}, x_{CO_2}, x_{N_2}, x_{H_2S}). \quad (3)$$

Mole fraction values for $N_2$ and $H_2S$ may then be calculated by solving $$C - \frac{P}{RTZ(T, P, x_{CH_4}, x_{C_2H_6}, x_{CO_2}, x_{N_2}, x_{H_2S})} = 0, \quad (4)$$

$$\eta - \tilde{\eta}(T, P, x_{CH_4}, x_{C_2H_6}, x_{CO_2}, x_{N_2}, x_{H_2S}) = 0, \quad (5)$$

and $$x_{CH_4} + x_{C_2H_6} + x_{CO_2} + x_{N_2} + x_{H_2S} - 1 = 0, \quad (6)$$

given that concentrations $Cx_{CH_4}$, $Cx_{C_2H_6}$ and $Cx_{CO_2}$ are known from calculations utilizing near infrared optical absorption measurements and η is the measurement for Joule-Thomson coefficient.

Figure 3A:
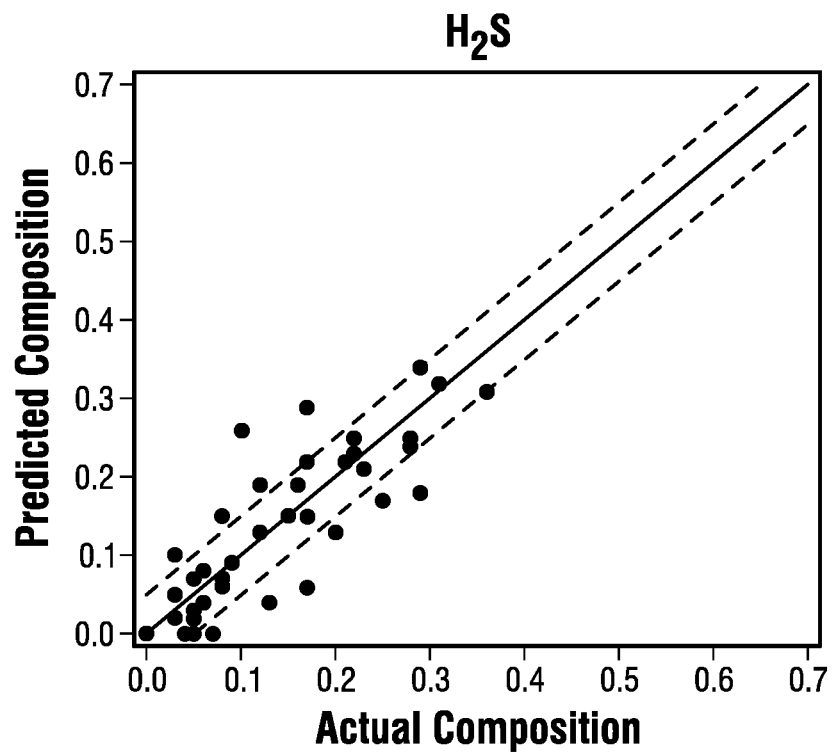
FIGS. 3a and 3b are plots of predicted compositions and actual compositions for hydrogen sulfide and nitrogen respectively.
Figure 3B:
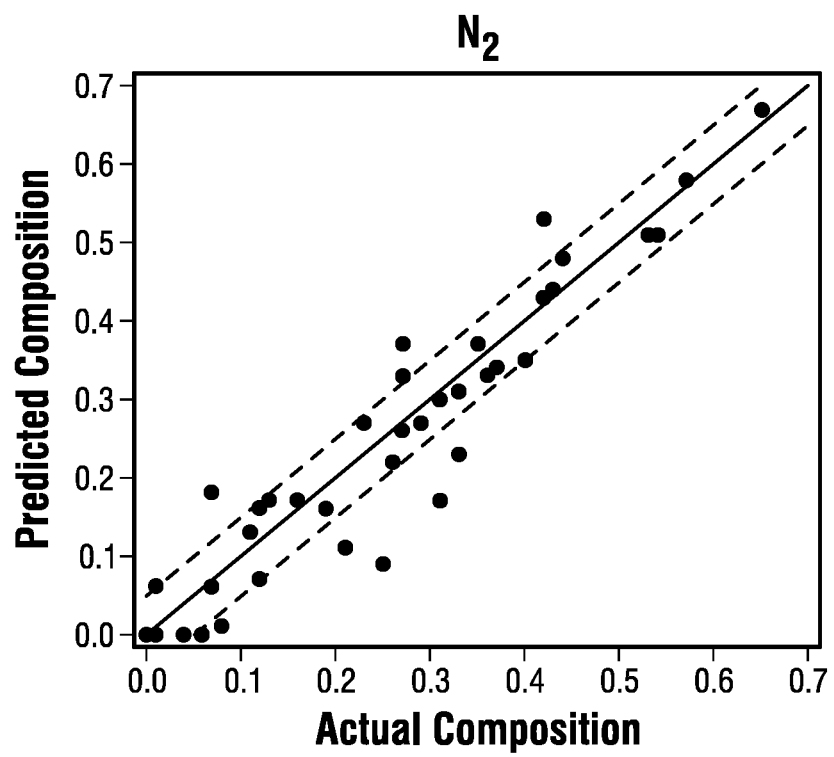
Figure 4A:
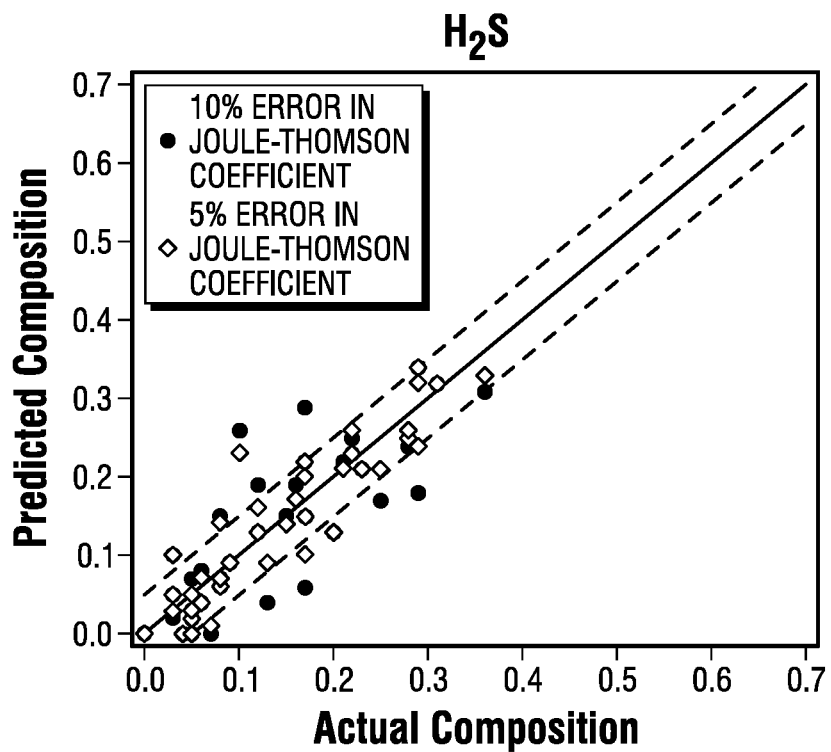
FIGS. 4a and 4b are plots of predicted compositions and actual compositions for hydrogen sulfide and nitrogen respectively, with different assumed errors in the Joule-Thomson coefficient measurement.
Figure 4B:
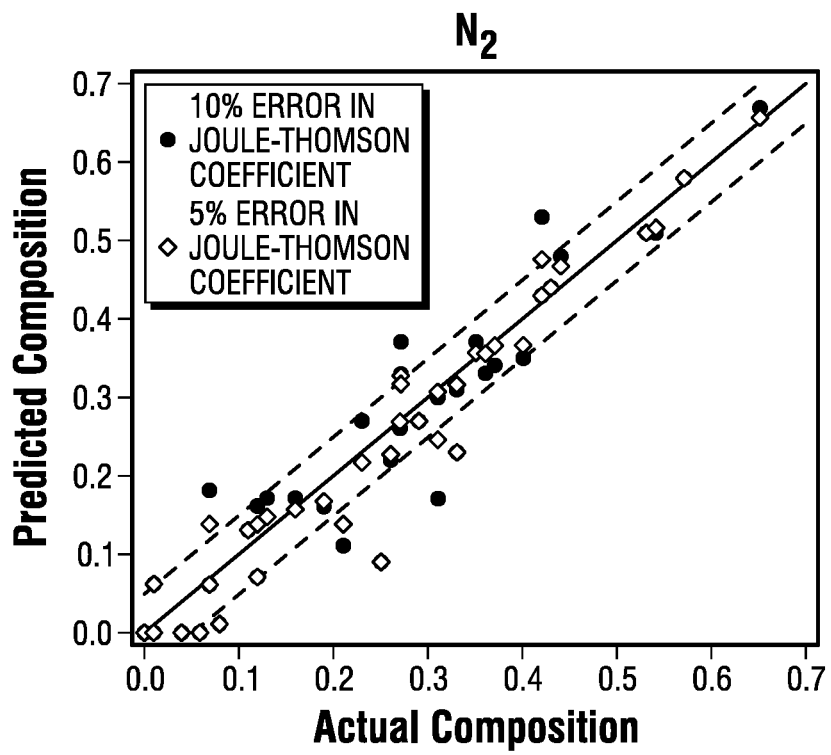

The predicted compositions generated by solving equations (4)-(6) are shown in FIGS. 3a and 3b which respectively compare the predicted $H_2S$ and $N_2$ concentrations with the actual ones. For the purpose of this computation, the measurement substitute for the Joule-Thomson coefficient i.e., the calculation with the noise added as stated previously, has been used. The presence of circles close to the solid black diagonal line indicates excellent agreement between the predictions and the actual concentrations. The black dashed lines indicate an error of ±0.05 (in mole fraction units). The root mean square errors between the predicted mole fractions of $N_2$ and $H_2S$ and the actual compositions of $N_2$ and $H_2S$ are 0.06 and 0.08 (in mole fraction units) respectively. This is larger than the typical error associated with $x_{CH_4}$, $x_{C_2H_6}$, and $x_{CO_2}$ determined using near-infrared absorption, because components $H_2S$ and $N_2$ are added here. Addition of these components also makes the concentration of the other components lower, thus increasing relative error. The test cases for which the errors in $x_{H_2S}$ and $x_{N_2}$ are high occur when the measurement error associated with η is also high. In fact, if the error in the Joule-Thomson coefficient is reduced by half, the root mean squre error reduces to 0.05 and 0.06 for $N_2$ and $H_2S$, respectively. These predictions are shown in FIGS. 4a and 4b.

For a down-hole system, and as discussed in more detail hereinafter, the sampled gas may be first collected in a sample chamber. If desired, the sample may be throttled down to lower pressures in more chambers. In one aspect, it can be seen that η may be measured from a few liters of gas stored in a chamber at formation pressure. In another aspect, it can be shown that relatively quick measurements (e.g., measurements completed in less than 15 minutes) can be made unaffected by the nonlinearities inherent in such measurements.

Consider the flow of gas across a porous disc. In one aspect, it may be useful to fix the minimum temperature change that will be measured or is measurable, and then compute an appropriate pressure change. The pressure change gives an estimate for the velocity, from which the suitability of Darcy's law may be evaluated, thus providing a self-consistency check. An estimate for flow rate is then obtained based on suitable geometry for the porous medium. It is then relevant to estimate the time scale for temperature stabilization, and then compute the total amount of gas required. In one aspect, this total volume may be small compared to the collection chamber volume, while requiring a flow rate that will enable a reasonably small stabilization time.

Since the pressure drop is smaller than the absolute pressure, say 10%, a pressure scale is given by $$P = \mu V L / k$$

where V is the characteristic velocity, L is the medium's length, and k is the permeability. For P=2 MPa, L=0.01 m, μ=0.018 mPa s, and k=0.001 μm², a velocity V=0.011 m s$^{-1}$ is obtained. Note that a permeability k of about 1 mD was chosen.

In order to ensure that the velocity is sufficiently low for Darcy's law to be applicable, a particle diameter may be estimated from the relationship $$k \approx \frac{\phi^m}{72} r_p^2$$

where $r_p$ is the pore radius, φ is the porosity and m is the cementation exponent derived from electrical formation factor. A pore radius $r_p$ of about 0.61 μm can be calculated for φ=0.4 and m=1.8. With a gas density of about 128 kg m⁻³, the Reynolds number based on pore diameter is 0.1, sufficiently small for non-Darcy effects to be negligible.

The time scale is dictated by two separate criteria. The first time scale is given by a pressure diffusion time scale $T_p$. The second time scale $T_{cT}$ is the convective transport of temperature as a result of the pressure drop. Other time scales, while present, are similar in magnitude to the other two. The pressure and convection time-scales may be shown to be respectively (c is the compressibility)

$$T_p = \frac{\phi \mu c L^2}{k} \text{ and} \tag{8}$$

$$T_{cT} = \frac{L^2 \mu}{kP} \frac{\rho_e C_{pe}}{\rho C_p} \tag{9}$$

where $\rho$ and $C_p$ are the density and the specific heat of the gas phase and $\rho_e$ and $C_{pe}$ are the effective density and specific heat respectively.

With $\phi=0.4$, $\mu=0.018$ mPa s, $c=0.05$ MPa⁻¹, $k=0.001$ μm², and $L=0.01$ m, consistent with previously used values, the pressure diffusion time $T_p \approx 36$ ms. For thermal time, an effective density of 2200 kg m⁻³ and specific heat of 1476 J kg⁻¹ K⁻¹ with a gas constant-pressure specific heat of 3230 J kg⁻¹ K⁻¹ are used. For these values, the thermal transport time $T_{cT}$ is 6-7 s. Tool storage effects will amplify this time scale, but the calculation illustrates that the measurement is possible in a relatively short time-frame.

For the velocity calculated above, for a diameter of 1 cm for the porous sample, a pragmatic flow rate of 0.8-0.9 mL s⁻¹ is obtained. A sampled volume of a few liters is sufficient. Assuming a time scale of 300 s to make the measurement, a total volume of about 250 mL would be required. Since the depletion from the sample volume is sufficiently small, a fairly stable $\Delta T$ across the porous disc should be obtained.

Figure 5:
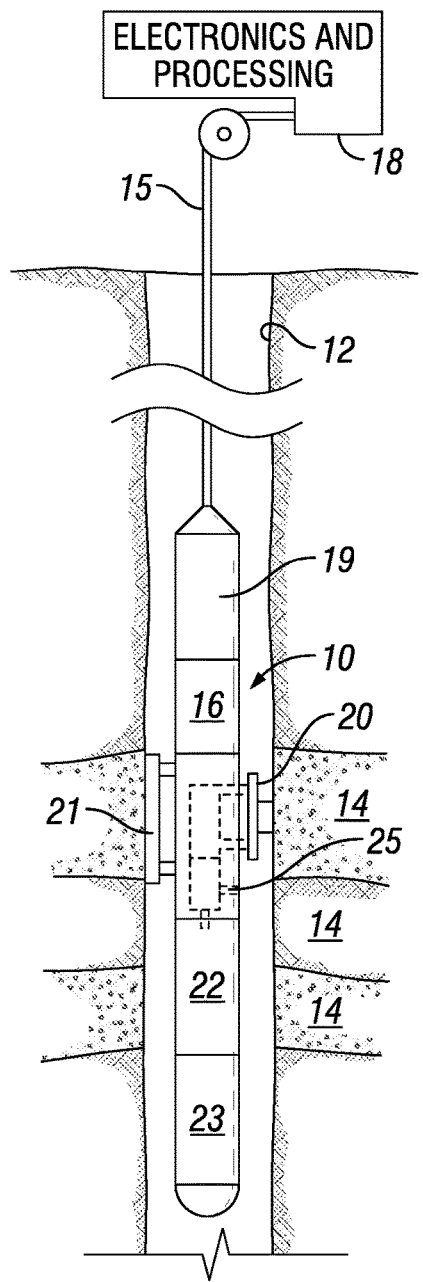
FIG. 5 is a block diagram of a downhole apparatus for measuring composition of gases flowing from a formation.
Figure 6:
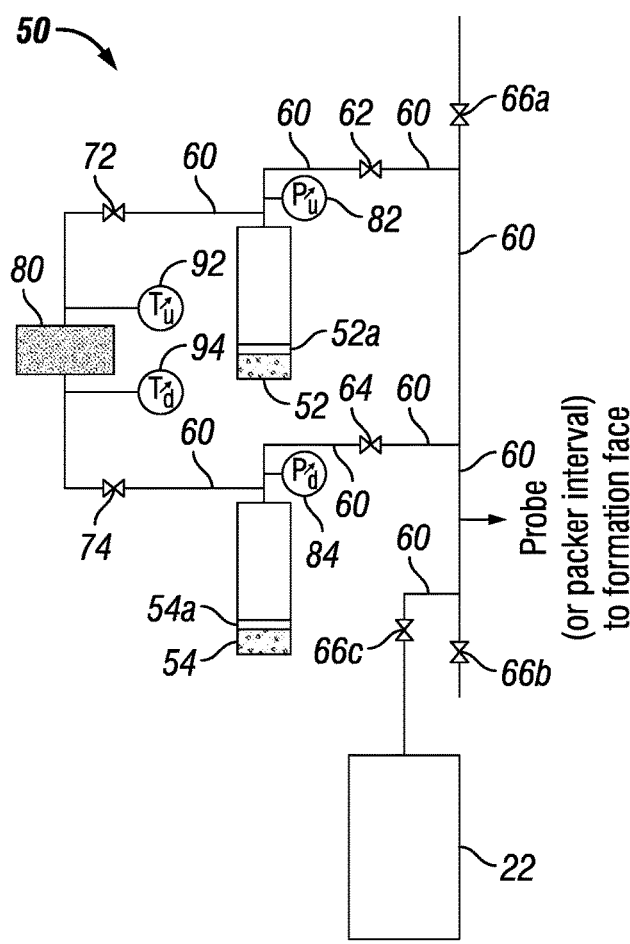
FIG. 6 is a block diagram of a portion of the apparatus of FIG. 5, useful for measuring Joule-Thomson coefficients for the gases.

Given the time-scales and the resulting stabilization times, an adaption to a formation testing tool for the purpose of measuring η (and thereby determining concentrations of H₂S and N₂ in a gas sample) is shown in FIGS. 5 and 6. As seen in FIG. 5, a tool 10 for testing earth formations and analyzing the composition of fluid (e.g., gas) from the formation 14 is seen. Tool 10 is suspended in a borehole (or wellbore—the two being used interchangeably herein) 12 from the lower end of a typical multiconductor cable 15 that is spooled in a usual fashion on a suitable winch (not shown) on the formation surface. On the surface, the cable 15 may be electrically coupled to an electrical control system 18 as described in more detail hereinafter. The tool includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the body. The fluid admitting assembly 20 is equipped for selectively sealing off or isolating selected portions of the wall of the borehole 12 such that pressure or fluid communication with the adjacent earth formation is established. Also included with tool 10 are a fluid analysis module 25 through which the obtained fluid flows. The fluid may thereafter be expelled through a port (not shown) or may be sent to one or more fluid collecting chambers 22 and 23 which may receive and retain the fluids obtained from the formation. In one aspect, the fluid analysis module may include an optical fluid analyzer such as shown and described in previously incorporated U.S. Pat. No. 4,994,671 to Safinya et al., U.S. Pat. No. 5,167,149 to Mullins et al., U.S. Pat. No. 5,201,220 to Mullins et al., U.S. Pat. No. 5,266,800 to Mullins et al., U.S. Pat. No. 5,331,156 to Hines et al., U.S. Pat. No. 5,859,430 to Mullins et al., Fujisawa, G., et al., "Near-infrared compositional analysis of gas and condensate reservoirs fluids at elevated pressures and temperatures", Applied Spectroscopy 56(12) pp. 1615-1620 (2002), and van Agthoven, M. A., et al., "Near-infrared spectral analysis of gas mixtures", Applied Spectroscopy 56(5) pp. 593-598 (2002), and also as known with respect to tools of Schlumberger Technology Corporation such as the In Situ Fluid Analyzer system for real-time downhole fluid analysis and the downhole fluid analysis or DFA tool. The optical fluid analyzer generally includes a light source that emits light in at least a portion of the near infrared (NIR) spectrum, a sample cell having at least one window through which the NIR rays from the light source are directed, and spectral detector elements for detecting the spectra of at least the NIR rays which are scattered and/or transmitted through the formation gases in the sample cell. The optical fluid analyzer may be used, among other things, to find the concentrations of $CH_4$, $C_2H_6$, and $CO_2$ using desired techniques. The processing required to determine the mole fractions may be accomplished down-hole utilizing a processor (not shown) and/or up-hole using processor 18 as described in more detail hereinafter.

In some embodiments, and as shown in FIG. 6, the tool 10 also includes a Joule-Thomson coefficient analysis module 50 which may be a separate module or may be part of or share elements of the fluid analysis module 25. The Joule-Thomson coefficient analysis module 50 may be under control of up-hole electronics and processing unit 18 as described in more detail hereinafter. In one embodiment, the Joule-Thomson coefficient analysis module 50 is provided with two chambers 52 and 54 with internal pistons 52a, 54a that may be controlled to cause the chambers 52 and 54 to empty or fill. The chambers 52 and 54 are coupled by pipes or tubes 60 to a source of formation gas via throttle valves 62, 64 which act as flow controllers. The formation gas may be provided directly from the formation or from a storage chamber such as a fluid (gas) collecting chamber 22 that may be kept at or near formation pressures. Various additional valves 66a, 66b, 66c are shown for controlling fluid flow through the pipes or tubes 60 to and from the chambers 52, 54 and 22. The chambers 52 and 54 are also coupled, via additional valves 72, 74 (and optionally through insulated conduits as in FIG. 2) to a porous element 80. Pressure sensor 82 is coupled to (upstream) chamber 52 to measure the gas pressure upstream of the porous element 80 while pressure sensor 84 is coupled to (downstream) chamber 54 to measure the gas pressure downstream of the porous disc 80. Temperature sensor 92 is likewise provided to measure the upstream temperature, while temperature sensor 94 is provided to measure the downstream temperature.

In some embodiments, pistons 52a, 54a are caused to bottom out, and the throttle valves 62 and 64 are opened (with valves 72 and 74 closed), thereby allowing gas from the formation (which may be stored in chamber 22 or another chamber) to enter the chambers 52, 54 and permitting pressure to build up in the chambers 52, 54. When, pressure sensors 82, 84 sense that desired upstream and downstream pressures are reached (e.g., an upstream pressure P, of say, 20 MPa, and a downstream pressure $P_d$ of say, 18 MPa), valves 62 and 64 are respectively shut, thereby establishing a closed system including chambers 52, 54, valves 72, 74, porous element 80, and the respective upstream and downstream sensors 82, 92 and 84, 94. At this point, valves 72 and 74 may be opened to permit gas flow via the pipes or tubes 60 through the porous element. After a period of time (dictated by the pressure and convection time-scales), the closed system approaches or reaches a steady-state, and the resulting ratio of the temperature difference to the pressure difference across the disc provides a determination of the Joule-Thomson coefficient i for the formation gas according to equation (1).

In some embodiments, the sizes of chambers 52 and 54, the pressures at which gas is kept in the chambers, and the parameters of the porous element 80 are selected so that a steady-state is reached in a desired time frame as discussed above. Thus, by way of example only and not by way of limitation, the porous element 80 may be a disc of thickness L=0.01 m, having a permeability k=1 mD and a porosity Φ=0.4. The material is preferably a relatively inert porous sintered ceramic, such as alumina. The material is available from Coors Tek of Golden, Colo., and Soilmoisture Equipment Corp. of Santa Barbara, Calif. Also, by way of example only and not by way of limitation, the chambers 52 and 54 may have a capacity of two liters.

In some embodiments, the same gas sample that is subjected to a near infrared optical fluid analysis, is utilized in the experiment involving chambers 52, 54, and porous element 80. The gas sample may be provided to the system with chambers 52, 54, and disc 80 before the sample is provided to the near infrared optical fluid analysis, or vice versa. Alternatively, a gas sample may be divided with some of the sample being provided to the system for determining its Joule-Thomson coefficient and other of the sample being provided to the near infrared optical fluid analysis.

In some embodiments, once an experiment has been conducted down-hole to find the Joule-Thomson coefficient of a gas sample, the pistons 52a, 54a may be activated, and various valves may be opened (and closed) to cause the gas to be jettisoned from the module or stored in a desired location. The system may then be utilized to conduct additional experiments with a different gas sample obtained at the same or a different location in the borehole.

Figure 7:
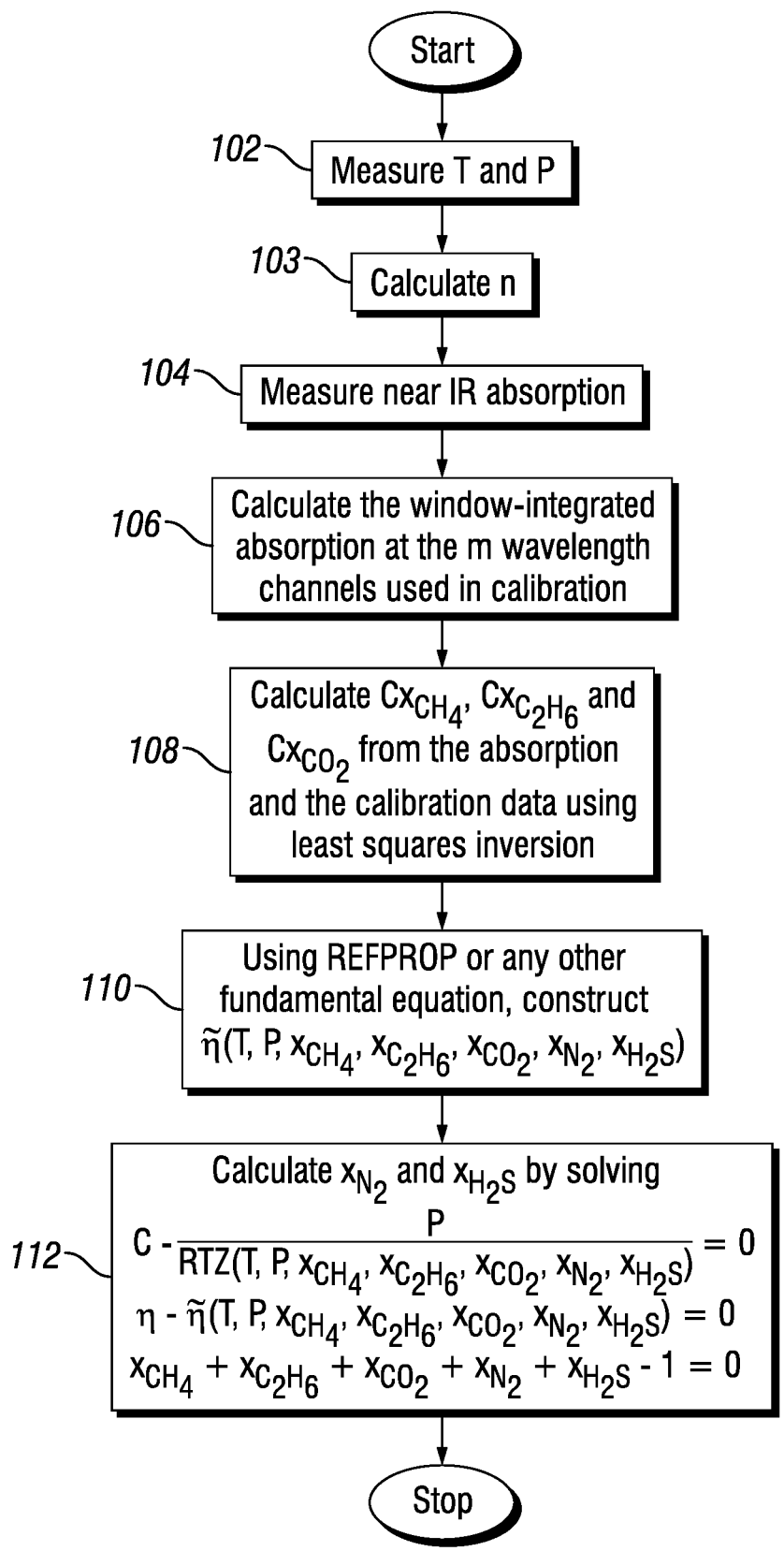
FIG. 7 is a flow diagram of a method for measuring down-hole the composition of gas.

Turning now to FIG. 7, one example is provided of a method of determining the mole fractions of $H_2S$ and $N_2$ in a gas sample. At 102, upstream and downstream temperature and pressure measurements are made down-hole with respect to a closed system in which gas sample is flowing as discussed above with reference to FIGS. 5 and 6. At 103, utilizing the change in temperature and pressure over time, the Joule-Thomson coefficient for the gas sample is calculated. At 104, an optical signal is measured for the gas sample as discussed above with reference to FIGS. 5 and 6. At 106, the optical signal is processed in order to calculate a window-integrated absorption at a plurality of wavelength channels used in calibration. At 108, the concentrations of $CH_4$, $C_2H_6$, and $CO_2$ are calculated from the absorption determinations and from the calibration data, e.g., using a least squares inversion. At 110, using REFPROP or any other fundamental equation, an expected or estimated Joule-Thomson coefficient for the gas sample is constructed as a function of temperature, pressure, and the mole fractions of the components of the gas sample; e.g., $\hat{\eta}(T, P, x_{CH_4}, x_{C_2H_6}, x_{CO_2}, x_{N_2}, x_{H_2S})$. Then, at 112, with knowledge of the previously measured and determined Joule-Thomson coefficient for the gas sample, and with knowledge of the previously determined concentrations of $CH_4$, $C_2H_6$, and $CO_2$, the mole fractions for $H_2S$ and $N_2$ are calculated by simultaneously solving equations (4)-(6). It is noted that in equations (4)-(6), there are three equations and three unknowns: the mole fractions of $H_2S$ and $N_2$ (i.e., $x_{H_2S}$, $x_{N_2}$), and C. Once C is determined, the mole fractions of $CH_4$, $C_2H_6$, and $CO_2$ are also obtained from the ratio of the individual concentrations to C.

The processor or processing system 18 that is provided may be located up-hole and/or down-hole and can be used to implement or perform any of the methods and processes for analyzing the composition of formation gases described above. The terms "processor" and "processing system" (hereinafter "processing system") should not be construed to limit the embodiments disclosed herein to any particular device type or system. The processing system may be a laptop computer, a desktop computer, or a mainframe computer. The processing system may also include a processor (e.g., a microprocessor, microcontroller, digital signal processor, or general purpose computer) for executing any of the methods and processes described above (e.g. processes 103, 106-112 in FIG. 7). The processing system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. This memory may be used to store, for example, fundamental equation and/or instructions for performing the processes described above.

Any of the methods and processes described above (e.g. processes 103, 106-112 in FIG. 7) can be implemented as computer program logic for use with the processing system. The computer program logic may be embodied in various forms, including a source code form or a computer executable form. Source code may include a series of computer program instructions in a variety of programming languages (e.g., an object code, an assembly language, or a high-level language such as FORTRAN, C, C++, PYTHON, or JAVA). Such computer instructions can be stored in a non-transitory computer readable medium (e.g. memory), and executed by the processing system. The computer instructions may be distributed in any form as a removable storage medium with accompanying printed or electronic documentation (e.g. shrink wrapped software), preloaded within a computer system (e.g. on system ROM, solid-state drive or a hard disk), or distributed from a server or electronic bulletin board over a communication system (e.g. the Internet or World Wide Web).

As used herein (including in the claims), a recitation in the general form of "at least one of [A] and [B]" (including, for example, "at least one of [A], [B], and [C]", "at least one of [A], [B], [C], and [D]", etc.) should be construed as disjunctive. For example, the recitation in the general form of "at least one of [A] and [B]" should be construed to include each of the following: (i) both [A] and [B] are present; (ii) [A] is present, but [B] is not, and (iii) [B] is present, but [A] is not.

There have been described and illustrated herein several embodiments of methods and apparatus for analyzing the composition of formation gases. While particular embodiments and aspects have been described, it is not intended that the disclosure be limited thereto, and it is intended that the claims be as broad in scope as the art will allow and that the specification be read likewise. Thus, while the methods and apparatus were described with reference to analyzing the composition of formation gases containing five specific gases, it will be appreciated that the methods can be readily extended to analyzing the composition of formations having additional, fewer and/or different gases. In addition, it will be appreciated that while specific apparatus were disclosed for measuring the Joule-Thomson coefficient of a gas, it will be appreciated that other apparatus could be utilized. Also, while methods were disclosed utilizing particular equations that related to mole fractions of components of the gas stream being measured, it will be appreciated that different equations could be utilized and could utilize other indications of the quantities or relative quantities of the gas stream components. Further, while particular near-infrared absorption measurement techniques and apparatus were described for the purpose of obtaining information regarding carbon-containing gas components of the gas being investigated, it will be appreciated that other techniques and apparatus could be utilized to gain information regarding certain components of the gas stream that may permit an ultimate determination of the make-up of the formation gas utilizing the Joule-Thomson coefficient measurements. It will therefore be appreciated by those skilled in the art that yet other modifications could be made. Accordingly, all such modifications are intended to be included within the scope of this disclosure as defined in the following claims. In the claims, means-plus-function clauses, if any, are intended to cover the structures described herein as performing the recited function and not only structural equivalents, but also equivalent structures. It is the express intention of the applicant not to invoke 35 U.S.C. § 112, paragraph 6 for any limitations of any of the claims herein, except for those in which the claim expressly uses the words 'means for' together with an associated function.

Moreover, it should be understood that any of the features described herein may be provided in any suitable combination.

What is claimed is:

1. A system for investigating gas from a formation traversing a borehole, the system comprising:
   a selectively extendible fluid admitting assembly configured to selectively isolate a portion of a wall of the borehole and establish fluid communication with the formation;
   first and second chambers in fluid communication with the fluid admitting assembly, the first and second chambers configured to receive a gas sample from the fluid admitting assembly;
   a porous element or a throttling valve in fluid communication with the first and second chambers, wherein the first chamber is upstream of the porous element or the throttling valve and the second chamber is downstream of the porous element or the throttling valve;
   an upstream pressure sensor fluidly coupled to the first chamber and configured to provide upstream pressure readings;
   a downstream pressure sensor fluidly coupled to the second chamber and configured to provide downstream pressure readings;
   an upstream temperature sensor coupled to the first chamber and configured to provide upstream temperature readings;
   a downstream temperature sensor coupled to the second chamber and configured to provide downstream temperature readings;
   control valves disposed between the at least one of (a) a porous element and (b) a throttling valve and the first and second chambers and between the first and second chambers and the fluid admitting assembly; and
   a processor configured to generate a determination of a Joule-Thomson coefficient ($\eta$) for the gas sample utilizing the readings from the upstream pressure sensor, the downstream pressure sensor, the upstream temperature sensor and the downstream temperature sensor.

2. The system of claim 1, wherein:
   the processor is configured to generate the determination of the Joule-Thomson coefficient according to $\eta = \Delta T/\Delta$, where $\Delta T/\Delta P \approx \partial T/\partial P$, the isenthalpic change in temperature T obtained from the readings of the upstream temperature sensor and the downstream temperature sensor relative to a change in pressure P obtained from the readings of the upstream pressure sensor and the downstream pressure sensor.

3. The system according to claim 2, wherein:
   the processor is configured to generate indications of a composition of the gas sample utilizing the Joule-Thomson coefficient $\eta$.

4. The system according to claim 3, further comprising:
   an optical fluid analyzer fluidly coupled to the fluid admitting assembly and adapted to detect near infrared spectra of the gas sample, the optical fluid analyzer coupled to the processor, wherein the processor is configured to utilize near infrared spectra to generate the indications of a composition of the gas sample.

5. The system according to claim 4, wherein:
   the processor is configured to utilize the near-infrared spectra to estimate concentration of methane ($CH_4$), ethane ($C_2H_6$) and carbon dioxide ($CO_2$) in the gas sample.

6. The system according claim 4, wherein:
   the processor is configured to generate the indications of a composition of a gas sample by solving equations $$C - \frac{P}{RTZ(T, P, x_{CH_4}, x_{C_2H_6}, x_{CO_2}, x_{N_2}, x_{H_2S})} = 0,$$

$$\eta - \tilde{\eta}(T, P, x_{CH_4}, x_{C_2H_6}, x_{CO_2}, x_{N_2}, x_{H_2S}) = 0, \text{ and}$$

$$x_{CH_4} + x_{C_2H_6} + x_{CO_2} + x_{N_2} + x_{H_2S} - 1 = 0,$$

where x is an indication of a mole fraction of an indicated constituent of the gas sample, $\tilde{\eta}$ is an estimated Joule-Thomson value for the gas sample, C is the total concentration of the gas sample, R is the gas constant, and Z is a compressibility factor of the gas sample.

7. A system for investigating gas from a formation traversing a borehole, comprising:
   a borehole tool including
   (i) a fluid admitting assembly configured to selectively isolate a portion of a wall of the borehole and establish fluid communication with the formation,
   (ii) an optical fluid analyzer in fluid communication with the fluid admitting assembly, the optical fluid analyzer configured to utilize a near infrared spectrum to analyze a gas sample obtained from the fluid admitting assembly, and
   (iii) a Joule-Thomson coefficient analyzer including
      (A) first and second chambers in fluid communication with the fluid admitting assembly,
      (B) a porous element or a throttling valve, in fluid communication with the first and second chambers,
      (C) pressure sensors coupled to the first and second chambers,
      (D) temperature sensors coupled to the first and second chambers, and
      (E) control valves coupled between the porous element and the first and second chambers and between the first and second chambers and the fluid admitting assembly; and at least one processor coupled to the Joule-Thomson coefficient analyzer and to the optical fluid analyzer and configured to (i) utilize readings from the pressure sensors and the temperature sensors to generate a determination of a Joule-Thomson coefficient ($\eta$) for the gas sample, (ii) find concentrations of methane ($CH_4$), ethane ($C_2H_6$) and carbon dioxide ($CO_2$) in the gas sample, and (iii) generate an indication of the concentration or mole fraction of at least one of hydrogen sulfide ($H_2S$) and nitrogen ($N_2$).

8. The system according to claim 7, wherein:
the at least one of hydrogen sulfide ($H_2S$) and nitrogen ($N_2$) comprises both hydrogen sulfide and nitrogen, and the at least one processor is configured to generate the indications of the mole fractions of methane, ethane, carbon dioxide, hydrogen sulfide and nitrogen by solving equations $$C - \frac{P}{RTZ(T, P, x_{CH_4}, x_{C_2H_6}, x_{CO_2}, x_{N_2}, x_{H_2S})} = 0,$$

$$\eta - \tilde{\eta}(T, P, x_{CH_4}, x_{C_2H_6}, x_{CO_2}, x_{N_2}, x_{H_2S}) = 0, \text{ and}$$

$$x_{CH_4} + x_{C_2H_6} + x_{CO_2} + x_{N_2} + x_{H_2S} - 1 = 0,$$

where x is an indication of a mole fraction of an indicated constituent of the gas sample, $\tilde{\eta}$ is an estimated Joule-Thomson value for the gas sample, C is the total concentration of the gas phase, R is the gas constant, and Z is a compressibility factor of the gas sample.

9. The system according to claim 8, wherein:
the first chamber is upstream of the porous element or throttling valve and the second chamber is downstream of the porous element or throttling valve;
the pressure sensors include an upstream pressure sensor fluidly coupled to the first chamber and providing upstream pressure readings, and a downstream pressure sensor fluidly coupled to the second chamber and providing downstream pressure readings;
the temperature sensors include an upstream temperature sensor coupled to the first chamber and configured to provide upstream temperature readings, and a downstream temperature sensor coupled to the second chamber and configured to provide downstream temperature readings.

10. The system according to claim 7, wherein the at least one processor includes an uphole processor located up-hole from the borehole tool.

11. The system according to claim 10, wherein the uphole processor communicates with the borehole tool via a cable.

12. A system for investigating gas from a formation traversing a borehole, comprising:
a borehole tool including (i) a fluid admitting assembly adapted to selectively isolate a portion of a wall of the borehole and establish fluid communication with the formation, (ii) an optical fluid analyzer in fluid communication with the fluid admitting assembly, the optical fluid analyzer configured to utilize a near infrared spectrum to analyze a gas sample obtained from the fluid admitting assembly, and (iii) a Joule-Thomson coefficient analyzer including first and second chambers in fluid communication with the fluid admitting assembly, (iv) a porous element or a throttling valve, in fluid communication with the first and second chambers, (v) pressure sensors coupled to the first and second chambers, (vi) temperature sensors coupled to the first and second chambers, and (vii) control valves coupled between the porous element and the first and second chambers and between the first and second chambers and the fluid admitting assembly; and
at least one processor coupled to the Joule-Thomson coefficient analyzer and to the optical fluid analyzer, the at least one processor being configured to (i) utilize readings from the pressure sensors and the temperature sensors and generate a determination of a Joule-Thomson coefficient ($\eta$) for the gas sample, and (ii) find a concentration and a mole fraction of at least one of methane ($CH_4$), ethane ($C_2H_6$), carbon dioxide ($CO_2$), hydrogen sulfide ($H_2S$) and nitrogen ($N_2$).

13. The system according to claim 12, wherein:
the at least one processor is configured to generate the indications of the mole fractions of methane, ethane, carbon dioxide, hydrogen sulfide and nitrogen by solving equations $$C - \frac{P}{RTZ(T, P, x_{CH_4}, x_{C_2H_6}, x_{CO_2}, x_{N_2}, x_{H_2S})} = 0,$$

$$\eta - \tilde{\eta}(T, P, x_{CH_4}, x_{C_2H_6}, x_{CO_2}, x_{N_2}, x_{H_2S}) = 0, \text{ and}$$

$$x_{CH_4} + x_{C_2H_6} + x_{CO_2} + x_{N_2} + x_{H_2S} - 1 = 0,$$

where x is an indication of a mole fraction of an indicated constituent of the gas sample, $\tilde{\eta}$ is an estimated Joule-Thomson value for the gas sample, C is the total concentration of the gas phase, R is the gas constant, and Z is a compressibility factor of the gas sample.

* * * * *